US008680283B2

(12) United States Patent
Beier et al.

(10) Patent No.: US 8,680,283 B2
(45) Date of Patent: Mar. 25, 2014

(54) PROCESS FOR THE PREPARATION OF 5-SUBSTITUTED 1-ALKYLTETRAZOLYL OXIME DERIVATIVES

(75) Inventors: Christian Beier, Bergisch Gladbach (DE); David Bernier, Lyons (FR); Pierre-Yves Coqueron, Lyons (FR); Philippe Desbordes, Lyons (FR); Christophe Dubost, Charbonnieres-les-Bains (FR); Norbert Lui, Odenthal (DE); Sergii Pazenok, Solingen (DE)

(73) Assignee: Bayer Intellectual Property GmbH (DE)

( * ) Notice: Subject to any disclaimer, the term of this patent is extended or adjusted under 35 U.S.C. 154(b) by 0 days.

(21) Appl. No.: 13/805,276

(22) PCT Filed: Jun. 21, 2011

(86) PCT No.: PCT/EP2011/060281

§ 371 (c)(1),
(2), (4) Date: Dec. 18, 2012

(87) PCT Pub. No.: WO2011/161076

PCT Pub. Date: Dec. 29, 2011

(65) Prior Publication Data

US 2013/0096311 A1 Apr. 18, 2013

Related U.S. Application Data

(60) Provisional application No. 61/357,768, filed on Jun. 23, 2010.

(30) Foreign Application Priority Data

Jun. 22, 2010 (EP) .................................... 10166852

(51) Int. Cl.
*C07D 401/00* (2006.01)

(52) U.S. Cl.
USPC ...................................................... 546/268.4

(58) Field of Classification Search
None
See application file for complete search history.

(56) References Cited

U.S. PATENT DOCUMENTS

| | | | | |
|---|---|---|---|---|
| 2005/0070439 | A1 | 3/2005 | Kobori et al. | 504/261 |
| 2005/0197373 | A1 | 9/2005 | Batt et al. | 514/381 |
| 2007/0105926 | A1 | 5/2007 | Kobori et al. | 514/381 |
| 2008/0132479 | A1 | 6/2008 | Sugawara et al. | 514/210.2 |
| 2009/0291936 | A1 | 11/2009 | Sugawara et al. | 514/210.2 |

FOREIGN PATENT DOCUMENTS

| | | |
|---|---|---|
| EP | 1426371 | 6/2004 |
| WO | WO 2005/079497 | 9/2005 |
| WO | WO 2007/007886 | 1/2007 |
| WO | WO 2010/000841 | 1/2010 |

OTHER PUBLICATIONS

U.S. Appl. No. 13/807,101 corresponding to PCT/EP2011/060675, having an International filing date of Jun. 27, 2011, published as WO 2012/000918 by Christian Beier et al.
International Search Report mailed Jul. 20, 2011 in corresponding International Application No. PCT/EP2011/060281.
Edward W. Thomas: "The Conversion of Secondary Amides to Tetrazoles with Trifluoromethanesulfonic Anhydride and Sodium Azide", Synthesis, Georg Thieme Verlag, Stuttgart, DE LNKD— DOI: 10.1055/S-1993-25934 , vol. 8, Jan. 1, 1993, pp. 767-768, XP007915458, ISSN: 0039-7881.

*Primary Examiner* — Janet L Andres
*Assistant Examiner* — Heidi Reese
(74) *Attorney, Agent, or Firm* — Ostrolenk Faber LLP

(57) ABSTRACT

The present invention relates to a process for the preparation of 5-substituted 1-alkyltetrazolyl oxime derivatives.

(I)

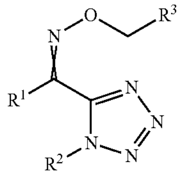

8 Claims, No Drawings

PROCESS FOR THE PREPARATION OF 5-SUBSTITUTED 1-ALKYLTETRAZOLYL OXIME DERIVATIVES

CROSS-REFERENCE TO RELATED APPLICATION(S)

The present application is a 35 U.S.C. §371 national phase conversion of PCT/EP2011/060281, filed on Jun. 21, 2011, which claims priority of European Application No. 10166852.3, filed on Jun. 22, 2010, and of U.S. Provisional Application No. 61/357,768, filed on Jun. 23, 2010. Applicants claim priority to each of the foregoing patent applications. The PCT International Application was published in the English language.

The present invention relates to a process for the preparation of 5-substituted 1-alkyltetrazolyl oxime derivatives.

5-Substituted 1-alkyltetrazolyl oxime derivatives are important intermediate compounds in active ingredient manufacture or are already fungicidally effective compounds (see e.g. WO 2010/000841). It is already known that 5-substituted 1-alkyltetrazoles can be prepared by lithiation of 1-methyltetrazole at −70° C. (cf. *Can. J. Chem.* 1971, 49, 2139-2142). However, the yield using the example of 5-benzoyl-1-methyltetrazole is only 41%. The 1-methyltetrazole used likewise has to be prepared in a multistage synthesis sequence. For an industrial reaction, the low temperatures and the expensive use of butyllithium are disadvantageous. Another process for the preparation of 5-benzoyl-1-methyltetrazole is known from *J. Amer. Chem. Soc.* 1963, 85, 2967-2976. Benzyl cyanide is reacted with ammonium azide to give 5-benzyltetrazole and then oxidized with chromium trioxide to give 5-benzoyltetrazole. The methylation to 5-benzoyl-1-methyltetrazole takes place with diazomethane. This synthesis route is likewise disadvantageous as regards safety and economical aspects. The preparation of 1-cyclohexyl-5-acetyltetrazole by reacting acetyl chloride over cyclohexyl isocyanide with subsequent reaction with hydrazoic acid is also known (cf. *Chem. Ber.* 1961, 94, 1116-1121). Hydrazoic acid is an unstable, extremely explosive and very toxic liquid which cannot be used on an industrial scale.

Starting from the known processes for the preparation of 5-substituted 1-alkyltetrazolyl oxime derivatives, the object now is how these can be produced safely and cost-effectively, so that the process can also be used for the industrial production of 5-substituted 1-alkyltetrazolyl oxime derivatives. A process to give 5-substituted 1-alkyltetrazolyl oxime derivatives has now been found which overcomes the aforementioned disadvantages.

The invention therefore provides a process for the preparation of 5-substituted 1-alkyltetrazolyl oxime derivatives of the general formula (I)

(I)

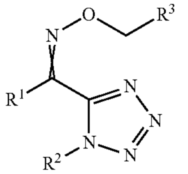

in which $R^1$ is alkyl, or phenyl optionally monosubstituted by halogen, cyano, nitro, $C_1$-$C_8$-alkyl, $C_1$-$C_8$-alkoxy, methylsulphonyl, trifluoromethyl or aryl, $R^2$ is $C_1$-$C_{12}$-alkyl, $C_1$-$C_{12}$-haloalkyl or an alkoxyalkyl of the formula -$[A\text{-}O]_m$—B, A is $C_2$-$C_4$-alkanediyl (alkylene), B is $C_1$-$C_6$-alkyl, m is 1 or 2, $R^3$ is a pyridinyl group ($Het^1$) or a thiazolyl group ($Het^2$)

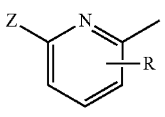

$Het^1$

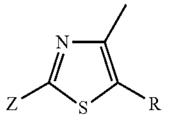

$Het^2$ in which

R is hydrogen or halogen,

Z is hydrogen, halogen, in each case substituted or unsubstituted $C_1$-$C_8$-alkyl, $C_3$-$C_8$-cycloalkyl, $C_2$-$C_8$-alkenyl, $C_2$-$C_8$-alkynyl, or the group —$N(R^a)C(=O)Q$, Q is hydrogen, in each case substituted or unsubstituted $C_1$-$C_8$-alkyl, $C_3$-$C_8$-cycloalkyl, $C_3$-$C_8$-cycloalkenyl-$C_1$-$C_8$-alkyl, $C_3$-$C_8$-halocycloalkyl having 1 to 5 halogen atoms, $C_3$-$C_8$-cycloalkyl-$C_1$-$C_8$-alkyl, $C_3$-$C_8$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_1$-$C_8$-halalkoxyalkyl having 1 to 5 halogen atoms, $C_2$-$C_8$-alkenyloxy, $C_2$-$C_8$-haloalkenyloxy having 1 to 5 halogen atoms $C_3$-$C_8$-alkynyloxy, $C_3$-$C_8$-haloalkynyloxy having 1 to 5 halogen atoms, $C_1$-$C_8$-alkylamino, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkinyloxyimino)-$C_1$-$C_6$-alkyl, (benzyloxyimino)-$C_1$-$C_6$-alkyl, $C_1$-$C_8$-alkylsulphenyl, arylsulphenyl, tri($C_1$-$C_8$-alkyl)silyl-$C_1$-$C_8$-alkyl, tri($C_1$-$C_8$-alkyl)silyloxy, tri($C_1$-$C_8$-alkyl)silyl-$C_3$-$C_8$-cycloalkyl, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl, $R^a$ is hydrogen, in each case substituted or unsubstituted $C_1$-$C_8$-alkyl, $C_3$-$C_8$-cycloalkyl, $C_2$-$C_8$-alkenyl, $C_2$-$C_8$-alkynyl, aryl, heterocyclyl, characterized in that (1) in a first step, oximes of the general formula (II)

(II)

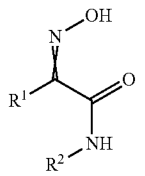

in which $R^1$ and $R^2$ have the meanings given above, are reacted with compounds of the general formula (III)

(III)

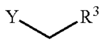

in which $R^3$ has the meanings given above and

Y is chlorine, bromine, iodine, mesylate or tosylate, and the oxime ethers of the general formula (IV) obtained in this way

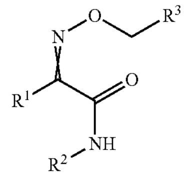

(IV)

in which $R^1$, $R^2$ and $R^3$ have the meanings given above, (2) are reacted in a second step with perfluoroalkylsulphonic acid esters ($R^4$—$SO_2$-Oalkyl) or anhydrides [($R^4$—$SO_2$)$_2$ O], and the compounds of the general formula (V) obtained in this way

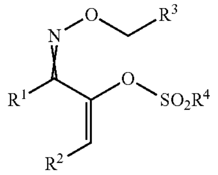

(V)

in which $R^1$, $R^2$ and $R^3$ have the meanings given above and $R^4$ is perfluoroalkyl, (3) are reacted in a third step with azides of the formula $R^5$—$N_3$.

The process according to the invention can be illustrated by the following scheme:

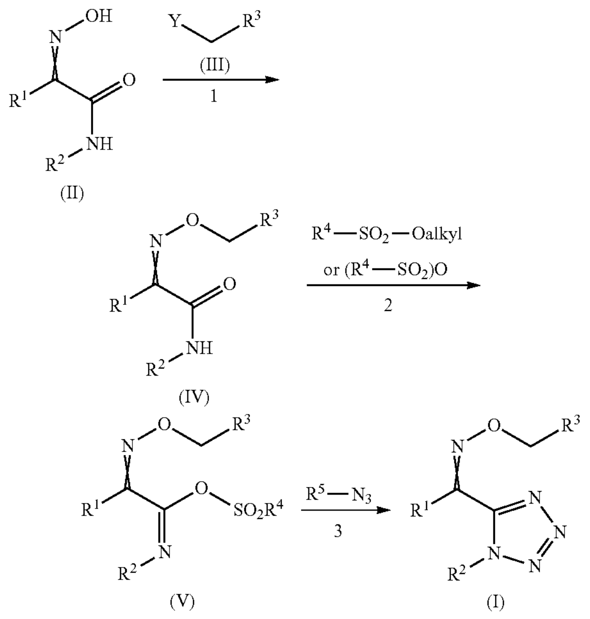

The oximes used as starting materials when carrying out the process according to the invention are generally defined by the formula (II).

$R^1$ is preferably $C_1$-$C_8$-alkyl, or phenyl optionally monosubstituted by fluorine, chlorine, bromine, iodine, cyano, nitro, $C_1$-$C_6$-alkyl, methylsulphonyl, trifluoromethyl or phenyl or naphthyl.

$R^1$ is particularly preferably $C_1$-$C_6$-alkyl, or phenyl optionally monosubstituted by fluorine, chlorine, $C_1$-$C_4$-alkyl or $C_1$-$C_3$-alkoxy.

$R^1$ is very particularly preferably methyl, ethyl, n-propyl, isopropyl, n-, s- or t-butyl, or is phenyl optionally monosubstituted by fluorine, chlorine, methyl, t-butyl, methoxy or ethoxy.

$R^1$ is especially preferably unsubstituted phenyl.

$R^2$ is preferably $C_1$-$C_8$-alkyl, $C_1$-$C_8$-haloalkyl or an alkoxyalkyl of the formula -[A-O]$_m$—B. $R^2$ is particularly preferably $C_1$-$C_4$-alkyl, $C_1$-$C_4$-haloalkyl or an alkoxyalkyl of the formula -[A-O]$_m$—B.

$R^2$ is very particularly preferably methyl, ethyl, trifluoromethyl, or an alkoxyalkyl of the formula -[A-O]$_m$—B.

$R^2$ is especially preferably methyl.

A is preferably —$(CH_2)_2$—, —$(CH_2)_3$—, —$CH(CH_3)$— or —$CH(CH_3)CH_2$—.

A is particularly preferably —$(CH_2)_2$— or —$CH(CH_3)CH_2$—.

A is very particularly preferably —$(CH_2)_2$—.

B is preferably $C_1$-$C_6$-alkyl.

B is particularly preferably $C_1$-$C_4$-alkyl.

B is very particularly preferably methyl or ethyl.

m is preferably 1.

Oximes of the formula (II) are known, e.g. commercially available, or can be prepared by known processes (cf. WO 99/50231).

The compounds further used as starting materials for carrying out the process according to the invention are defined by the formula (III).

$R^3$ is preferably a pyridinyl group ($Het^1$)

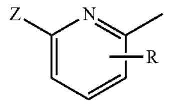

$Het^1$ $R^3$ is also preferably a thiazolyl group ($Het^2$)

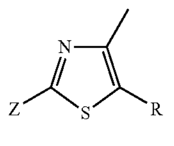

$Het^2$

R is preferably hydrogen, fluorine, chlorine or bromine

R is particularly preferably hydrogen.

Z is preferably hydrogen, halogen, in each case substituted or unsubstituted $C_1$-$C_6$-alkyl, $C_3$-$C_6$-cycloalkyl, $C_2$-$C_8$-alkenyl, $C_2$-$C_8$-alkynyl, or the group —N($R^a$)C(═O)Q.

Z is particularly preferably fluorine, chlorine, bromine, in each case substituted or unsubstituted $C_1$-$C_4$-alkyl, $C_2$-$C_8$-alkenyl, $C_2$-$C_8$-alkynyl, or the group —N($R^a$)C(═O)Q.

Z is very particularly preferably fluorine, chlorine, bromine, in each case substituted or unsubstituted $C_2$-$C_8$-alkenyl, $C_2$-$C_8$-alkynyl, or the group —N($R^a$)C(═O)Q.

Q is preferably hydrogen, in each case substituted or unsubstituted $C_1$-$C_6$-alkyl, $C_3$-$C_6$-cycloalkyl, $C_3$-$C_6$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_1$-$C_8$-haloalkoxyalkyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl.

Q is particularly preferably in each case substituted or unsubstituted $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms.

Q is very particularly preferably $C_1$-$C_8$-alkoxy, $C_1$-$C_8$-haloalkoxy having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms.

Q is especially preferably tert-butyloxy or but-3-yn-1-yloxy.

$R^a$ is preferably hydrogen or substituted or unsubstituted $C_1$-$C_6$-alkyl.

$R^a$ is particularly preferably hydrogen.

Y is preferably chlorine, bromine, iodine, mesylate, tosylate, triflate.

Y is particularly preferably chlorine, bromine, mesylate, tosylate.

Y is very particularly preferably chlorine and bromine.

The compounds of the formula (III) are known or can be prepared by known processes.

The perfluoroalkylsulphonic acid esters or anhydrides further used as starting materials when carrying out the process according to the invention are generally described by the formulae $R^4$—$SO_2$Oalkyl or $(R^4—SO_2)_2O$.

$R^4$ is preferably trifluoromethyl, pentafluoroethyl, perfluorobutyl or perfluorooctyl.

$R^4$ is particularly preferably trifluoromethyl.

Preference is given to using trifluoromethanesulphonic anhydride.

Perfluoroalkylsulphonic acid esters and anhydrides are known, e.g. commercially available.

The azides further used as starting materials when carrying out the process according to the invention are generally designed by the formula $R^5$—$N_3$.

$R^5$ is preferably sodium, potassium, tetrabutylammonium, trimethylsilyl, diphenylphosphoryl.

$R^5$ is particularly preferably sodium or trimethylsilyl.

$R^5$ is very particularly preferably sodium.

Azides of the formula $R^5$—$N_3$ are known, e.g. commercially available, or can be prepared by known processes.

The compounds of the formulae (I) may be present either in pure form or else as mixtures of different possible isomeric forms, in particular of stereoisomers, such as E and Z, threo and erythro, and also optical isomers, such as R and S isomers or atropisomers, but in some cases also of tautomers. Both the E and also the Z isomers, and also the threo and erythro, and the optical isomers, any desired mixtures of these isomers, and the possible tautomeric forms are encompassed by this application. In particular, the possibility of E or Z isomers on the double bond of the oxime group may be mentioned.

In the definitions of the symbols given in the formulae above, collective terms have been used which generally representatively stand for the following substituents:

Halogen stands for fluorine, chlorine, bromine or iodine.

A heteroatom can be nitrogen, oxygen or sulphur.

Unless stated otherwise, a group or a substituted radical can be substituted by one or more of the following groups or atoms, where, in the case of multiple substitution, the substituents may be identical or different: halogen, nitro, hydroxy, cyano, amino, sulphenyl, pentafluoro-$\lambda^6$-sulphenyl, formyl, carbaldehyde-O—($C_1$-$C_8$-alkyl) oxime, formyloxy, formylamino, carbamoyl, N-hydroxycarbamoyl, formylamino, (hydroxyimino)-$C_1$-$C_6$-alkyl, $C_1$-$C_8$-alkyl, tri($C_1$-$C_8$-alkyl)silyl, tri($C_1$-$C_8$-alkyl)silyl-$C_1$-$C_8$-alkyl, $C_3$-$C_8$-cycloalkyl, tri($C_1$-$C_8$-alkyl)silyl-$C_3$-$C_8$-cycloalkyl, $C_1$-$C_8$-haloalkyl having 1 to 5 halogen atoms, $C_3$-$C_8$-halocycloalkyl having 1 to 5 halogen atoms, $C_2$-$C_8$-alkenyl, $C_3$-$C_8$-cycloalkenyl, $C_2$-$C_8$-alkynyl, $C_2$-$C_8$-alkenyloxy, $C_2$-$C_8$-alkynyloxy, $C_1$-$C_8$-alkylamino, di-$C_1$-$C_8$-alkylamino, $C_1$-$C_8$-alkoxy, $C_1$-$C_8$-haloalkoxy having 1 to 5 halogen atoms, $C_1$-$C_8$-alkylsulphenyl, $C_1$-$C_8$-halonalkylsulphenyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, $C_1$-$C_8$-alkylcarbonyl, $C_1$-$C_8$-haloalkylcarbonyl having 1 to 5 halogen atoms, $C_1$-$C_8$-alkylcarbamoyl, di-$C_1$-$C_8$-alkylcarbamoyl, N—$C_1$-$C_8$-alkyloxycarbamoyl, $C_1$-$C_8$-alkoxycarbamoyl, N—$C_1$-$C_8$-alkyl-$C_1$-$C_8$-alkoxycarbamoyl, $C_1$-$C_8$-alkoxycarbonyl, $C_1$-$C_8$-haloalkoxycarbonyl having 1 to 5 halogen atoms, $C_1$-$C_8$-alkylcarbonyloxy, $C_1$-$C_8$-haloalkylcarbonyloxy having 1 to 5 halogen atoms, $C_1$-$C_8$-alkylcarbonylamino, $C_1$-$C_8$-haloalkylcarbonylamino having 1 to 5 halogen atoms, $C_1$-$C_8$-alkoxycarbonylamino, $C_1$-$C_8$-haloalkoxycarbonylamino having 1 to 5 halogen atoms, $C_1$-$C_8$-alkylaminocarbonyloxy, di-$C_1$-$C_8$-alkylaminocarbonyloxy, $C_1$-$C_{89}$-alkyloxycarbonyloxy, $C_1$-$C_8$-alkylsulphenyl, $C_1$-$C_8$-haloalkylsulphenyl having 1 to 5 halogen atoms, $C_1$-$C_8$-alkylsulphynyl, $C_1$-$C_8$-haloalkylsulphynyl having 1 to 5 halogen atoms, $C_1$-$C_8$-alkylsulphonyl, $C_1$-$C_8$-haloalkylsulphonyl having 1 to 5 halogen atoms, $C_1$-$C_8$-alkylaminosulphamoyl, di-$C_1$-$C_8$-alkylaminosulphamoyl, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-haloalkoxyalkyl having 1 to 5 halogen atoms, aryl, heterocyclyl, benzyloxy, benzylsulphenyl, benzylamino, phenoxy, phenylsulphenyl or phenylamino.

Aryl is phenyl or naphthyl.

Heterocyclyl is a saturated or unsaturated 4-, 5-, 6-, 7-, 8-, 9-, 10- or 11-ring-member-containing ring having up to 4 heteroatoms.

The first reaction step (1) preferably takes place in the presence of a base. Suitable bases are organic and inorganic bases which are usually used in such reactions. Preference is given to using bases which are selected for example from the group consisting of alcoholates, acetates, fluorides, phosphates, carbonates and hydrogencarbonates of alkali metal or alkaline earth metals. Preference is also given to tertiary amines, such as trimethylamine, triethylamine, tributylamine, N,N-dimethylaniline, N,N-dimethylbenzylamine, pyridine, alkylpyridines, such as 2-methyl-5-ethylpyridine, N-methylpiperidine, N-methylpyrrolidone, N,N-dimethylaminopyridine, diazabicyclooctane (DABCO), diazabicyclononene (DBN) and diazabicycloundecene (DBU). Particular preference is given here to sodium methanolate, potassium-tert-butanolate, caesium carbonate, sodium hydride.

The molar ratio of base to the compound of the formula (II) used is for example 0.8-10, preferably 0.9-6, particularly preferably 1.0-3. The use of larger amounts of base is possible in principle, but does not lead to any preferred embodiment and is disadvantageous for reasons of cost.

The ratio of the oxime of the formula (II) used to the compound of the formula (III) used can vary. Preferably, the ratio of oxime of the formula (II) to the compound of the formula (III) used is in the range from 0.6:1 to 1:2, in particular in the range from 0.8:1 to 1:1.5, specifically from 0.9:1.1 to 1:1.4.

The oxime ethers of the formula (IV) obtained in step (1) can either be isolated or be further reacted directly in situ.

In step (1), it is preferred according to the invention to introduce as initial charge the oxime of the formula (II) either without solvent, i.e. without dilution, or in a suitable solvent and then to add the compound of the general formula (III), which is optionally dissolved in a suitable solvent. It is also possible to introduce as initial charge the compound of the general formula (III) and to meter in the oxime of the formula (II) as salt. A parallel metered addition of both components is also possible.

In step (1), the reaction is preferably carried out in a solvent. The solvents are preferably used in an amount such that the reaction mixture remains readily stirrable throughout the entire process. Suitable solvents for carrying out the process according to the invention are all organic solvents inert under the reaction conditions. According to the invention, solvents are also understood as meaning mixtures of pure solvents.

Solvents suitable according to the invention are in particular ethers (e.g. ethyl propyl ether, methyl tert-butyl ether, n-butyl ether, anisole, phenetol, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; aliphatic, cycloaliphatic or aromatic hydrocarbons (e.g. pentane, hexane, heptane, octane, nonane, such as so-called "white spirits" with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, xylene); halogenated hydrocarbons, such as chlorobenzene, dichlorobenzene, dichloromethane, chloroform, tetrachloromethane, dichloroethane or trichloroethane; esters (e.g. methyl, ethyl, butyl, isobutyl acetate, dimethyl, dibutyl or ethylene carbonate, propylene carbonate); amides (e.g. hexamethylene phosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine); nitriles, such as acetonitrile, propionitrile, n- or isobutyronitrile or benzonitrile; ketones such as acetone or mixtures thereof.

For the reaction according to the invention, the solvents used are preferably aromatic and/or aliphatic hydrocarbons, amides, nitriles, ethers, in particular toluene, acetonitrile, THF, methylene chloride.

The process according to the invention can generally be carried out in vacuo, at atmospheric pressure or superatmospheric pressure.

The process according to the invention in step (1) takes place at temperatures of −20 to +150° C., preferably at temperatures from −10 to +70° C.

The second and third reaction step (2 and 3) is optionally carried out in the presence of a base. However, the steps can also be carried out without base. The reaction preferably takes place in the presence of a base. Suitable bases are organic and inorganic bases which are usually used in such reactions. Preference is given to using bases which are selected for example from the group of tertiary amines, such as trimethylamine, triethylamine, tributylamine, N,N-dimethylaniline, N,N-dimethylbenzylamine, pyridine, alkylpyridines, such as 2,6-dimethylpyridine, 2-methyl-5-ethylpyridine, N-methylpiperidine, N-methylpyrrolidone, N,N-dimethylaminopyridine, diazabicyclooctane (DABCO), diazabicyclononene (DBN) and diazabicycloundecene (DBU).

The compound of the formula (V) obtained in step (2) is not isolated, but further reacted directly in situ.

The molar ratio of base to the compound of the formula (IV) used is for example 0.8-10, preferably 0.9-6, particularly preferably 1.0-3. The use of larger amounts of base is possible in principle, but does not lead to a preferred embodiment and is disadvantageous for reasons of cost.

The ratio of oxime ether of the formula (V) to the azide of the formula $R^5$—$N_3$ can vary. A significant excess is not critical for the reaction, but is uneconomic. Preferably, the ratio of oxime ether of the formula (IV) to the azide of the formula $R^5$—$N_3$ is in the range from 1:1 to 1:3, in particular in the range from 1:1 to 1:2, specifically in the range from 1:1.0 to 1:1.3.

In the second and third step (2 and 3), the reaction is preferably carried out in a solvent. The solvents are preferably used in an amount such that the reaction mixture remains readily stirrable throughout the entire process. Suitable solvents for carrying out the process according to the invention are all organic solvents inert under the reaction conditions. According to the invention, solvents is also understood as meaning mixtures of pure solvents.

Solvents suitable according to the invention are in particular ethers (e.g. ethyl propyl ether, methyl tert-butyl ether, n-butyl ether, anisole, phenetol, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; aliphatic, cycloaliphatic or aromatic hydrocarbons (e.g. pentane, hexane, heptane, octane, nonane, such as so-called "white spirits" with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, xylene); halogenated hydrocarbons, such as chlorobenzene, dichlorobenzene, dichloromethane, chloroform, tetrachloromethane, dichloroethane or trichloroethane; esters (e.g. methyl, ethyl, butyl, isobutyl acetate, dimethyl, dibutyl or ethylene carbonate, propylene carbonate); amides (e.g. hexamethylene phosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine); nitriles, such as acetonitrile, propionitrile, n- or isobutyronitrile or benzonitrile; or mixtures thereof.

For the reaction according to the invention, the solvents preferably used are aromatic and/or aliphatic hydrocarbons, amides, nitriles, ethers, in particular toluene, acetonitrile, THF, methylene chloride, or mixtures thereof.

The process according to the invention can generally be carried out in vacuo, at atmospheric pressure or at superatmospheric pressure.

The process according to the invention in step (1) takes place at temperatures of −30 to +100° C., preferably at temperatures of −10 to +70° C.

The present invention is illustrated in more detail by reference to the examples below, without thereby limiting the invention thereto.

PREPARATION EXAMPLES

Preparation of the Starting Material: 2-(hydroxyimino)-N-methyl-2-phenylacetamide

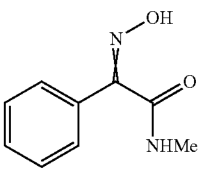 [SMILES: CNC(=O)C(=NO)c1ccccc1]

Hydroxylamine hydrochloride (5.96 g, 2.5 eq.) was added to a solution of N-methyl-2-oxo-2-phenylacetamide (5.6 g, 34.3 mmol) in pyridine (25 ml). After stirring for 10 h at room temperature, the excess pyridine was removed in vacuo and the residue was taken up in 250 ml of dichloromethane. The organic phase was washed with 200 ml of water and then again with aqueous hydrochloric acid (0.1 M, 250 ml). The precipitated solid was filtered off, giving 2-(hydroxyimino)-N-methyl-2-phenylacetamide as a yellow solid (2.31 g, pure Z isomer). The filtrate was concentrated by evaporation in vacuo. This gave 4.50 g of 2-(hydroxyimino)-N-methyl-2-phenylacetamide (Z/E=mixture of isomers) as a yellow solid.

$^1$H-NMR (400 MHz, DMSO-$d_6$/DMSO-$d_5$=2.50, water signal at δ=3.33; for the sake of simplicity, only the signals of the main diastereoisomer were shown): δ=11.51 (s, 1H), 8.40 (br. q, J=4.4 Hz, 1H), 7.55-7.35 (m, 5H), 2.74 (d, J=4.4 Hz, 3H).

Example 1

Preparation of tert-butyl {6-[({[2-(methylamino)-2-oxo-1-phenylethylidene]amino}oxy)methyl]pyridin-2-yl}carbamate

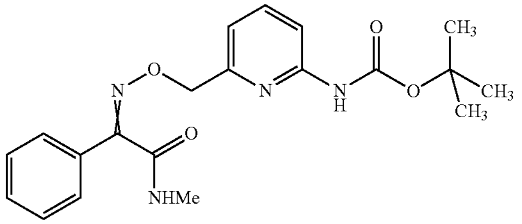 [SMILES: CNC(=O)C(=NOCc1cccc(NC(=O)OC(C)(C)C)n1)c1ccccc1]

37.4 g (114 mmol) of caesium carbonate and 0.91 g, (5.47 mmol) of potassium iodide were added to a solution of 10.7 g (60.1 mmol) of 2-(hydroxyimino)-N-methyl-2-phenylacetamide (81:19 mixture of the Z and E diastereoisomers) and 13.3 g (54.7 mmol) of tert-butyl [6-(chloromethyl)pyridin-2-yl]carbamate in 100 ml of acetonitrile: DMF 75:25. After stirring for 3 h at room temperature, the mixture was concentrated by evaporation in vacuo and the residue was admixed with 250 ml of ethyl acetate. Then, 500 ml of water were added, the phases were separated and the aqueous phase was extracted again with 250 ml of ethyl acetate. The combined organic phases were dried with $MgSO_4$ and concentrated by evaporation in vacuo. This gave 16.8 g (95% purity; 89:11 mixture of Z and E isomers) of tert-butyl {6-[({[2-(methylamino)-2-oxo-1-phenylethylidene]amino}oxy)methyl]pyridin-2-yl}carbamate.

$^1$H-NMR (400 MHz, $CDCl_3$/TMS, water signal at δ=1.56; for the sake of simplicity, only the signals of the main diastereoisomers were shown): δ=7.82 (d, J=8.1 Hz, 1H), 7.70-7.60 (m, 3H), 7.45-7.30 (m, 3H), 7.18 (br. s, 1H), 7.04 (d, 1H), 6.36 (br. q., J=5.0 Hz, 1H), 5.23 (s, 2H), 3.02 (d, J=5.0 Hz, 3H), 1.52 (s, 9H).

Example 2

But-3-yn-1-yl{6-[({[(1-methyl-1H-tetrazol-5-yl)(phenyl)methylene]amino}oxy)methyl]pyridin-2-yl}carbamate

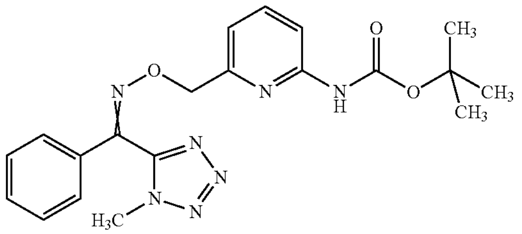 [SMILES: Cn1nnnc1C(=NOCc1cccc(NC(=O)OC(C)(C)C)n1)c1ccccc1]

At −10° C., trifluoromethanesulphonic anhydride (42 μl, 1.5 eq.) was added to a solution of 63 mg (0.16 mmol) of tert-butyl{6-[({[2-(methylamino)-2-oxo-1-phenylethylidene]amino}oxy)methyl]pyridin-2-yl}carbamate (36:64 mixture of Z and E diastereoisomers) and pyridine (53 μl, 4 eq.) in acetonitrile (1.6 ml). After warming to room temperature, the mixture was stirred for a further 1 h at 50° C. and then cooled again to room temperature. Then, 32 mg of sodium azide were added and the mixture was stirred again at 50° C. for one hour. The mixture was cooled to room temperature and a sample was analyzed using LCMS. The sample comprises 87% of the expected tert-butyl {6-[({[(1-methyl-1H-tetrazol-5-yl)(phenyl)methylene]amino}oxy)methyl]pyridin-2-yl}carbamate (36:64 mixture of Z and E diastereoisomers).

$^1$H-NMR (400 MHz, DMSO-$d_6$/DMSO-$d_5$=2.50, water signal at δ=3.33): δ=9.84 (s, 1H), 7-80-7.70 (m, 2H), 7.60-7.40 (m, 5H), 7.05-7.00 (m, 1H), 5.28 (s, 2H), 4.07 (s, 3H), 1.47 (s, 9H).

Example 3

But-3-yn-1-yl {6-[({[2-(methylamino)-2-oxo-1-phenylethylidene]amino}oxy)methyl]pyridin-2-yl}carbamate

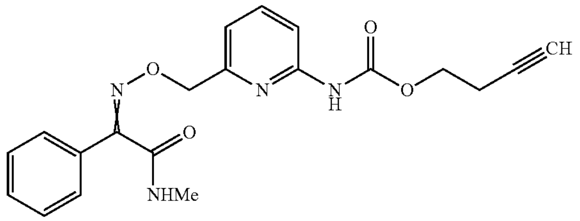 [SMILES: C#CCCOC(=O)Nc1cccc(CON=C(C(=O)NC)c2ccccc2)n1]

49 mg (1.22 mmol) of sodium hydride were added to a solution of 200 mg (1.12 mmol) of 2-(hydroxyimino)-N-methyl-2-phenylacetamide (only Z diastereoisomer in 5 ml of DMF, and the suspension was stirred for 30 minutes at room temperature. Then, a solution of 268 mg (1.12 mmol) of but-3-in-1-yl[6-(chloromethyl)pyridin-2-yl]carbamate in 5 ml was added. The mixture was stirred for 3.5 hours at room temperature and then poured into 70 ml of water and admixed with 50 ml of AcOEt. The organic phase was separated off and dried over $MgSO_4$. After removing the solvent, this gave 388 mg (95% purity, 88:12 mixture of Z and E diastereoisomers) of but-3-yn-1-yl{6-[({[2-(methylamino)-2-oxo-1-phenylethylidene]amino}oxy)methyl]pyridin-2-yl}-carbamate.

Isomer separation: a 100 mg mixture of Z and E stereoisomers (91:9 mixture) was recrystallized in 1 ml of acetonitrile. This gave pure Z isomer following filtration (58 mg, 100% Z isomer, melting point=154-156° C.).

$^1$H-NMR (400 MHz, $CDCl_3$/TMS, water signal at δ=1.56; for the sake of simplicity, only the signals of the main diastereoisomers were shown): δ=7.84 (d, J=8.0 Hz, 1H), 7.75-7.59 (m, 3H), 7.55-7.30 (m, 4H), 7.18 (br. s, 1H), 7.09 (d, J=7.6 Hz 1H), 6.29 (br. q., J=5.0 Hz, 1H), 5.24 (s, 2H), 4.29 (t, J=6.7 Hz, 2H), 3.02 (d, J=5.0 Hz, 3H), 2.59 (td, J=6.7 and 2.6 Hz, 2H), 2.02 (t, J=2.6 Hz, 1H).

Example 4

But-3-yn-1-yl {6-[({[(1-methyl-1H-tetrazol-5-yl)(phenyl)methylene]amino}oxy)methyl]-pyridin-2-yl}carbamate

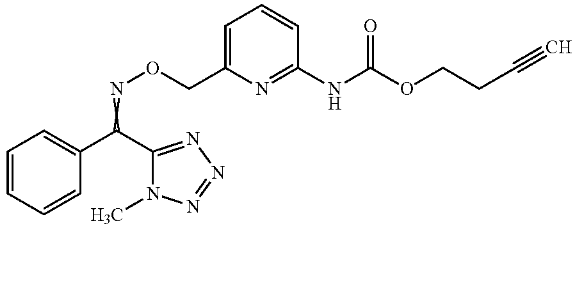 [SMILES: C#CCCOC(=O)Nc1cccc(CON=C(c2ccccc2)c2nnnn2C)n1]

With ice cooling, 85 μl of trifluoromethanesulphonic anhydride were added to a solution of 100 mg (0.25 mmol) of but-3-yn-1-yl(Z)-{6-[({[2-(methylamino)-2-oxo-1-phenylethylidene]amino}oxy)methyl]pyridin-2-yl}carbamate (only Z diastereoisomer) and pyridine (81 μl, 4 eq.) in acetonitrile (2 ml). The mixture was heated at 50° C. for 2 h and then cooled to room temperature. Then, 49 mg of sodium azide were added and the mixture was stirred again at 50° C. for 2 h. The homogeneous orange solution was then cooled to room temperature and filtered over silica gel, and the silica gel filter layer was washed with 50 ml of EtOAc. The combined organic phases were concentrated by evaporation in vacuo, giving 87 mg (84% purity) of (Z)-but-3-yn-1-yl{6-[({[(1-methyl-1H-tetrazol-5-yl)(phenyl)methylene]amino}oxy)methyl]pyridin-2-yl}carbamate.

$^1$H-NMR (400 MHz, DMSO-$d_6$/DMSO-$d_5$=2.50, water signal at δ=3.33): δ=10.30 (s, 1H), 7-84-7.76 (m, 2H), 7.58-7.40 (m, 5H), 7.08-7.02 (m, 1H), 5.29 (s, 2H), 4.18 (t, J=6.7 Hz, 2H), 4.05 (s, 3H), 2.91 (t, J=2.7 Hz, 1H), 2.56 (td, J=6.5 and 2.6 Hz, 2H).

The invention claimed is:

1. Process for the preparation of 5-substituted 1-alkyltetrazolyl oxime derivatives of the general formula (I)

(I)

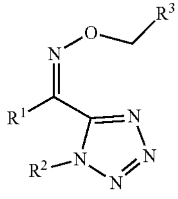

in which $R^1$ is alkyl, or phenyl optionally monosubstituted by halogen, cyano, nitro, $C_1$-$C_8$-alkyl, $C_1$-$C_8$-alkoxy, methylsulphonyl, trifluoromethyl or aryl, $R^2$ is $C_1$-$C_{12}$-alkyl, $C_1$-$C_{12}$-haloalkyl or an alkoxyalkyl of the formula -[A-O]$_m$—B, A is $C_2$-$C_4$-alkanediyl (alkylene), B is $C_1$-$C_6$-alkyl, m is 1 or 2, $R^3$ is a pyridinyl group (Het$^1$) or a thiazolyl group (Het$^2$)

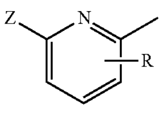

Het$^1$

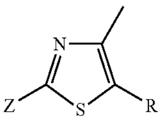

Het$^2$ in which

R is hydrogen or halogen,

Z is hydrogen, halogen, in each case substituted or unsubstituted $C_1$-$C_8$-alkyl, $C_3$-$C_8$-cycloalkyl, $C_2$-$C_8$-alkenyl, $C_2$-$C_8$-alkynyl, or the group—N($R^a$)C(=O)Q, Q is hydrogen, in each case substituted or unsubstituted $C_1$-$C_8$-alkyl, $C_3$-$C_8$-cycloalkyl, $C_3$-$C_8$-cycloalkenyl-$C_1$-$C_8$-alkyl, $C_3$-$C_8$-halocycloalkyl having 1 to 5 halogen atoms, $C_3$-$C_8$-cycloalkyl-$C_1$-$C_8$-alkyl, $C_3$-$C_8$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$-alkoxy, $C_1$-$C_8$-haloalkoxy having 1 to 5 halogen atoms, $C_1$-$C_8$-haloalkoxyalkyl having 1 to 5 halogen atoms, $C_2$-$C_8$-alkenyloxy, $C_2$-$C_8$-haloalkenyloxy having 1 to 5 halogen atoms $C_3$-$C_8$-alkynyloxy, $C_3$-$C_8$-haloalkynyloxy having 1 to 5 halogen atoms, $C_1$-$C_8$-alkylamino, ($C_1$-$C_6$-alkoxyimino)-$C_1$-$C_6$-alkyl, ($C_1$-$C_6$-alkenyloxyimino)-$C_1$-$C_6$-alkyl, ($C_1$-$C_6$-alkinyloxyimino)-$C_1$-$C_6$-alkyl, (benzyloxyimino)-$C_1$-$C_6$-alkyl, $C_1$-$C_8$-alkylsulphenyl, arylsulphenyl, tri($C_1$-$C_8$-alkyl)silyl-$C_1$-$C_8$-alkyl, tri($C_1$-$C_8$-alkyl)silyloxy, tri($C_1$-$C_8$alkyl)silyl-$C_3$-$C_8$-cycloalkyl, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl, $R^a$ is hydrogen, in each case substituted or unsubstituted $C_1$-$C_8$-alkyl, $C_3$-$C_8$-cycloalkyl, $C_2$-$C_8$-alkenyl, $C_2$-$C_8$-alkynyl, aryl, heterocyclyl, wherein the compounds of formula (I) may be present in pure form or else as mixtures of different possible isomeric forms;

characterized in that (1) in a first step, oximes of the general formula (II)

(II)

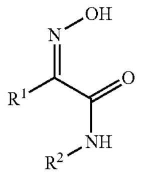

in which $R^1$ and $R^2$ have the meanings given above, are reacted with compounds of the general formula (III)

(III)

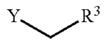

in which $R^3$ has the meanings given above and

Y is chlorine, bromine, iodine, mesylate or tosylate, and the oxime ethers of the general formula (IV) obtained in this way (IV)

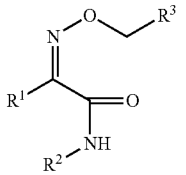

in which $R^1$, $R^2$ and $R^3$ have the meanings given above, (2) are reacted in a second step with perfluoroalkylsulphonic acid esters ($R^4$—$SO_2$—Oalkyl) or anhydrides [($R^4$-$SO_2$)$_2$O], and the compounds of the general formula (V) obtained in this way (V)

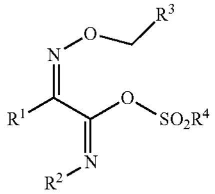

in which $R^1$, $R^2$ and $R^3$ have the meanings given above and $R^4$ is perfluoroalkyl, (3) are reacted in a third step with azides of the formula $R^5$—$N_3$ wherein $R^5$ is selected from the group consisting of sodium, potassium, tetrabutylammonium, trimethylsilyl and disphenylphosphoryl.

2. Process according to claim 1, characterized in that oximes of the formula (II) and compounds of the formula (III) are used, in which $R^1$ is $C_1$-$C_8$-alkyl, or phenyl optionally monosubstituted by fluorine, chlorine, bromine, iodine, cyano, nitro, $C_1$-$C_6$-alkyl, methylsulphonyl, trifluoromethyl or phenyl or naphthyl, $R^2$ is $C_1$-$C_8$-alkyl, $C_1$-$C_8$-haloalkyl or an alkoxyalkyl of the formula -[A-O]$_m$—B, A is —$(CH_2)_2$—, —$(CH_2)_3$—, —$CH(CH_3)$— or —$CH(CH_3)CH_2$—, B is $C_1$-$C_6$-alkyl, m is 1, $R^3$ is a pyridinyl group (Het[1]) or a thiazolyl group (Het[2])

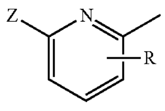

Het[1]

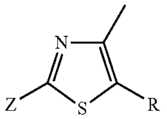

Het[2]

in which

R is hydrogen, fluorine, chlorine or bromine,

Z is hydrogen, halogen, in each case substituted or unsubstituted $C_1$-$C_6$-alkyl, $C_3$-$C_6$-cycloalkyl, $C_2$-$C_8$-alkenyl, $C_2$-$C_8$-alkynyl, or the group—$N(R^a)C(=O)Q$, Q is hydrogen, in each case substituted or unsubstituted $C_1$-$C_6$-alkyl, $C_3$-$C_6$-cycloalkyl, $C_3$-$C_6$-cycloalkenyl, $C_2$-$C_8$-alkenyl, $C_2$-$C_8$-haloalkenyl having 1 to 5 halogen atoms, $C_2$-$C_8$-alkynyl, $C_2$-$C_8$-haloalkynyl having 1 to 5 halogen atoms, $C_1$-$C_8$alkoxy, $C_1$-$C_8$-haloalkoxy having 1 to 5 halogen atoms, $C_1$-$C_8$-haloalkoxyalkyl having 1 to 5 halogen atoms, $C_2$-$C_8$-alkenyloxy, $C_2$-$C_8$-haloalkenyloxy having 1 to 5 halogen atoms, $C_3$-$C_8$-alkynyloxy, $C_3$-$C_8$-haloalkynyloxy having 1 to 5 halogen atoms, aryl, phenoxy, phenoxyalkyl, benzyloxy, heterocyclyl, $C_5$-$C_{12}$-bicycloalkyl, $C_5$-$C_{12}$-bicycloalkenyl, benzo-fused $C_5$-$C_{12}$-carbocyclyl, $R^a$ is hydrogen or substituted or unsubstituted $C_1$-$C_6$-alkyl, Y is chlorine, bromine, iodine, mesylate, tosylate, triflate.

3. Process according to claim 1, characterized in that step (1) is carried out in the presence of a base.

4. Process according to claim 3, characterized in that the molar ratio of base to the oxime of the formula (II) used is 0.8-10.

5. Process according to claim 1, characterized in that step (1) is carried out in a solvent.

6. Process according to claim 1, characterized in that step (2) and step (3) are carried out in the presence of a base.

7. Process according to claim 6, characterized in that the molar ratio of base to the compound of the formula (IV) used is 0.8-10.

8. Process according to claim 1, characterized in that the compound of the formula (V) obtained in step (2) is not isolated, but is further reacted in situ.

* * * * *